United States Patent [19]

Sayles

[11] Patent Number: 5,100,625
[45] Date of Patent: Mar. 31, 1992

[54] APPARATUS FOR TESTING CANDIDATE ROCKET NOZZLE MATERIALS

[75] Inventor: David C. Sayles, Huntsville, Ala.

[73] Assignee: The United States of America as represented by the Secretary of the Army, Washington, D.C.

[21] Appl. No.: 625,561

[22] Filed: Dec. 7, 1990

[51] Int. Cl.$^5$ .................. G01N 31/12; F02K 9/97
[52] U.S. Cl. .................. 422/78; 60/200.1; 60/267; 73/35; 73/116; 156/173; 422/68.1; 436/2
[58] Field of Search ........... 422/68.1, 78; 73/35 R, 73/116; 60/200.1, 266, 267; 436/2; 156/173

[56] References Cited

U.S. PATENT DOCUMENTS

| | | | |
|---|---|---|---|
| 3,630,449 | 12/1971 | Butler | 60/267 |
| 4,981,033 | 1/1991 | Yang | 73/116 |
| 4,990,312 | 2/1991 | Rucker et al. | 422/78 |

*Primary Examiner*—Jill A. Johnston
*Attorney, Agent, or Firm*—Freddie M. Bush; Robert L. Broad

[57] ABSTRACT

An apparatus for testing candidate rocket nozzle materials includes an elongated member having a combustion chamber extending therethrough, with an inlet at the forward end of the combustion chamber for admitting and igniting a gaseous mixture of hydrogen and oxygen and a nozzle secured to the combustion chamber at the aft end thereof. The nozzle is made of wafers or petals of materials to be tested, with the wafers being secured together at the edges thereof and having a configuration such that the wafers in transverse cross section form a polygon which has an area which increases with distance from the combustion chamber.

6 Claims, 1 Drawing Sheet

APPARATUS FOR TESTING CANDIDATE ROCKET NOZZLE MATERIALS

DEDICATORY CLAUSE

The invention described herein may be manufactured, used and licensed by or for the Government for governmental purposes without the payment to me of any royalties thereon.

BACKGROUND OF THE INVENTION

1. Field of the Invention

This invention relates to apparatus for testing candidate rocket nozzle materials.

2. Prior Art

No really satisfactory method has existed for testing materials for suitability for use in rocket nozzles. In the past such testing was done by making the rocket nozzle from the material to be tested and then firing the rocket. If the material survived it was deemed to be suitable. Unfortunately, this type of test was not a controlled test, such that one could determine the temperature at which the material failed.

SUMMARY OF THE INVENTION

Apparatus for testing candidate rocket nozzle materials wherein an elongated member having a combustion chamber extending therethrough, with means at the forward end of the combustion chamber for admitting and igniting a gaseous mixture of hydrogen and oxygen and a nozzle secured to the combustion chamber at the aft end thereof. The nozzle is made of wafers of materials to be tested, with the wafers being secured together at the edges thereof and having a configuration such that the wafers in transverse cross section form a polygon which has an area which increases with distance from the combustion chamber.

DETAILED DESCRIPTION OF THE INVENTION

Figure 1:
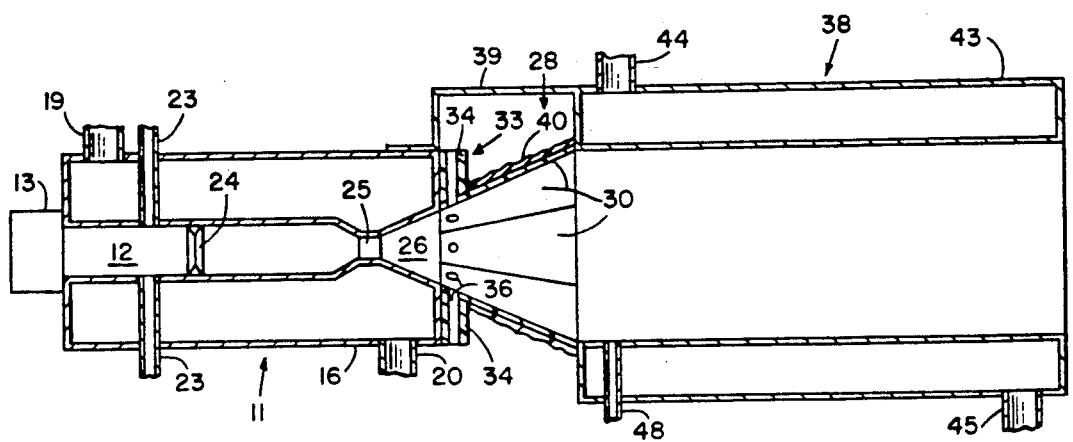
FIG. 1 is a cross sectional view showing the positioning of the various parts making up the invention.

Referring now in detail to the drawing, there is shown a rocket nozzle candidate testing assembly made up of an elongated member 11 having therein a combustion chamber 12 which extends from one end of the member 11 to the other. The forward end of the member 11 is provided with means for injecting and igniting a mixture of gaseous hydrogen and oxygen, this means being shown schematically and indicated by reference numeral 13 in FIG. 1. Structure for so injecting and igniting a combustible gas is well known. The member 11 is provided with a water jacket 16 so that the combustion chamber 12 can be cooled to the desired degree. The jacket 16 is provided with a water inlet 19 and a water outlet 20.

The combustion chamber 12 is fitted with a plurality of water injection ports connected to supply lines 23 so that the hydrogen/oxygen combustion products can be cooled to the desired temperature.

The combustion chamber 12 is equipped with a ring 24 which serves to induce turbulence in the combustion products in order to promote a more uniform temperature throughout the gaseous combustion products.

Figure 2:
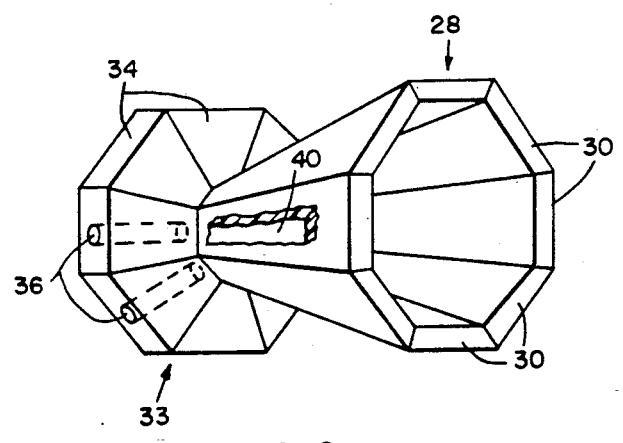
FIG. 2 is an enlarged perspective view showing the configuration of the nozzle to be tested.

The aft end of the combustion chamber is provided with an exit throat 25 through which the combustion gases enter an expansion zone 26 at the end of the member 11. The combustion gases are expanded in the expansion zone and enter a nozzle 28 which is made of the materials to be tested for suitability for use as rocket nozzle materials. This nozzle 28 is best shown in FIG. 2.

The nozzle 28 is made up of a number of petals 30 machined from different types of carbon-carbon composite wafers of nozzle candidate materials. The wafers or petals 30 are so configured that the assembled wafers in cross section form a polygon which increases in area with distance from the combustion chamber. In the drawing, eight of such wafers are shown.

The assembled wafers or petals 30 extend into a central opening in a flange member 33 which, in this case, is made up of eight pieces 34 cut from the same carbon-carbon materials and assembled to form the flange member 33 as shown.

The assembled wafers or petals 30 and the pieces 34 are bonded together with a sealant which is carbonized in a known manner prior to testing. In addition, graphite pins 36 (FIG. 2) extend through the flange pieces 34 into apertures in the petals 30 and are cemented in place to provide a mechanical interlock between each petal 30 and its associated flange piece 34.

After assembly of the petals 30 and the flange pieces 34, the nozzle is wet wound with a graphite T-40 which has been impregnated with a carbonizable resin. The entire assembly is then carbonized in a known manner. The overwrap is again impregnated and carbonized.

A diffuser 38, attached to the elongated member 11 by a bracket 39, is provided for carrying combustion products away from the nozzle 28. The diffuser is provided with a water jacket 43 with an inlet 44 and an outlet 45 for cooling water. The diffuser 38 is also provided with an inlet 48 through which a nitrogen purge can be admitted to protect the nozzle from atmospheric oxygen during the cooldown period after testing.

Chromal-alumel thermocouples (not shown) are positioned at various locations in the nozzle to determine the temperatures of the petals 30 during the test. By using this structure, the materials can be tested at various temperatures. For example, the temperatures can be increased as the test is carried out, so that one will readily know the temperature at which the material failed. Usually, the materials will fail by erosion or recession. When one of the petals 30 has failed, a comparison of the remaining petals can be made by observing the amount of recession of each.

What is claimed is:

1. Apparatus for testing candidate rocket nozzle materials, comprising
   a. an elongated member having therein a combustion chamber extending from a forward end of the member to an aft end, said member having at the forward end thereof an inlet for admitting a mixture of gaseous hydrogen and oxygen to the combustion chamber,
   b. means attached to the forward end of the member for igniting the gaseous mixture in the combustion chamber,
   c. a nozzle secured to the aft end of the member in communication with the combustion chamber; said nozzle being made of petals of materials to be tested; said petals being secured together at edges thereof and having a configuration such that when assembled, the petals in transverse cross section form a polygon which has an area which increases with distance from the combustion chamber, and d. a tubular diffuser secured to the aft end of the member in communication with the nozzle for expanding combustion products from the nozzle.

2. The apparatus of claim 1 wherein the diffuser is provided with a water jacket for cooling said diffuser.

3. The apparatus of claim 1 wherein the petals making up the nozzle are secured together with a char-forming resin.

4. The apparatus of claim 3 wherein the nozzle is wrapped with a graphite tow impregnated with a resin in carbonized form.

5. The apparatus of claim 4 wherein the forward end of the nozzle is provided with a flange made from the materials to be tested, said flange being secured to the aft end of the member to hold the nozzle in communication with said combustion chamber.

6. The apparatus of claim 5 wherein the member is provided with inlets for injection of water into the combustion chamber to cool said combustion products to a desired temperature.

* * * * *